(12) United States Patent
Haque

(10) Patent No.: US 10,045,875 B2
(45) Date of Patent: Aug. 14, 2018

(54) VEST TO PROVIDE DECOMPRESSION AND TRACTION FOR SPINE AND METHOD OF USE

(71) Applicant: Ekramul Haque, Lees Summit, MO (US)

(72) Inventor: Ekramul Haque, Lees Summit, MO (US)

( * ) Notice: Subject to any disclaimer, the term of this patent is extended or adjusted under 35 U.S.C. 154(b) by 289 days.

(21) Appl. No.: 15/145,058

(22) Filed: May 3, 2016

(65) Prior Publication Data
US 2017/0319370 A1    Nov. 9, 2017

(51) Int. Cl.
- *A61F 5/00* (2006.01)
- *A61F 5/02* (2006.01)
- *A61F 5/048* (2006.01)
- *A61F 5/01* (2006.01)

(52) U.S. Cl.
CPC .............. *A61F 5/026* (2013.01); *A61F 5/048* (2013.01); *A61F 2005/0197* (2013.01)

(58) Field of Classification Search
CPC .......... A61F 5/026; A61F 5/028; A61F 5/048; A61F 5/042
See application file for complete search history.

(56) References Cited

U.S. PATENT DOCUMENTS

| | | | |
|---|---|---|---|
| 1,589,670 A * | 6/1926 | Vartia | A61F 5/024 128/DIG. 20 |
| 2,835,247 A * | 5/1958 | Stabhole | A61F 5/024 602/19 |
| 3,420,230 A * | 1/1969 | Ballard | A61F 5/024 602/19 |
| 4,715,362 A * | 12/1987 | Scott | A61F 5/024 602/19 |
| 5,651,764 A * | 7/1997 | Chiu | A61F 5/026 602/19 |
| 5,876,361 A * | 3/1999 | Harris | A61F 5/024 602/19 |
| 6,280,405 B1 * | 8/2001 | Broselid | A61F 5/024 128/874 |
| 2004/0073150 A1 * | 4/2004 | Roballey | A61F 5/024 602/36 |
| 2004/0204666 A1 * | 10/2004 | Marsh | A61F 5/055 602/18 |
| 2006/0149178 A1 * | 7/2006 | Dunfee | A61F 5/024 602/19 |
| 2015/0257916 A1 * | 9/2015 | Brown | A61F 5/042 602/36 |
| 2016/0296361 A1 * | 10/2016 | Leake | A61F 5/048 |

* cited by examiner

*Primary Examiner* — Kristen Matter

(57) ABSTRACT

"Vest to Provide Decompression and Traction for Spine and Method of Use" consists of (1) a thoracic top belt (2) a waist bottom belt, each belt having provision of independent tightening (3) an elastic band connecting both belts, thus making a single vest and ((4) a turn buckle mounted in the back of wearer parallel to sine.)

The turn buckle integrally but detachably positioned against the top belt and bottom belt provides upward lifting force to the thorax via the top belt and the downward force to the lumbar via the bottom belt, providing the decompression and traction to the spine.

5 Claims, 2 Drawing Sheets

VEST TO PROVIDE DECOMPRESSION AND TRACTION FOR SPINE AND METHOD OF USE

TECHNICAL FIELD OF INVENTION

The invention relates to an under-garment or an over-garment wearable apparatus for use by (1) patients suffering from various spinal diseases which are treated by a mechanical spinal decompression method and (2) persons who want to support and protect the spine from injury during spinal load bearing activities. The apparatus can be used during different positional status of the user; standing, walking, running, sitting, lying, and changing positions such as, from squatting to standing and vice versa. The decompression and the traction to the spine can be used by the user without any help from others. Presently, there is no vest apparatus or method available for use during different positional status of the user mentioned above.

BACKGROUND OF THE INVENTION

About 80 percent of adults experience lower back pain (LBP) at some point in their lifetimes. About 20 percent affected by acute LBP develop chronic LBP with persistent symptoms at one year. In 2010, a study ranked LBP as the third most burdensome conditions in the U.S. in terms of mortality or poor health, only ischemic heart disease and chronic obstructive pulmonary disease ranking higher. Back pain is the #2 reason adults visit doctors and #1 reason for orthopedic visits. Each year million people go to the doctor for chronic back pain which leaves 2.4 million Americans chronically disabled and another 2.4 million temporarily disabled. Bulging and herniated discs, central and foraminal stenosis, epidural lipomatosis, hypertrophies of the facet joints and ligamenta flava, to name a few only are the main reasons of LBP for many people. Back pain is a worldwide problem.

The inventor has been suffering from the LBP for some time caused by diseases including bulging disc, low grade anterolisthesis, central and bi-lateral foraminal stenosis, lipomatosis, hypertrophy of facet joints and ligamenta flava. He was advised spinal decompression physical therapy; underwent the therapy and got temporary relief. During the therapy, he lied flat on his back on a table top bed, his chest was restrained—from movement by a belt wrapped around and tied to the table, while another belt wrapped around his lumbar was pulled by a motorized cable exerting a tensile force on the spine. This device is big and only usable under restricted conditions. Intermittent but regular use of decompression and traction is presently not very practical, because each time the patients who do not have home traction device have to go to physical therapists. Besides, home traction devices are big and not readily usable. The present invention is a vest which contains an embedded detachable decompression and traction device in it and a means to measure the force of decompression and traction. The use of lumbar supports in the form of wide elastic bands which can be tightened to provide support to the lower back and abdominal muscles to prevent low back pain is widespread. These lumbar supports are not very useful because of lack of strength and their inability to (1) share a large portion of downward axial loads imposed on the spine and (2) provide decompression relief whoever wants it.

BRIEF SUMMARY OF THE INVENTION

The problems outlined above are in large measure solved by the "Vest to Provide Decompression and Traction for Spine and Method of Use" in accordance with the present invention. In accordance with the present invention, an equipment and method of its use are developed to provide decompression and traction to the spine to relieve the pressure on the spine in general, and its components such as nerves, nerve roots, discs, vertebrae and facet joints in particular. Decompression which means reduction of compressive load on the spine and its components allow more space to be created within the spinal foramens and inter vertebral discs. So, decompression gives relief for many patients. However, since no decompression device is presently available for use as and when and where desired, many patients cannot take advantage of the relief decompression gives. Many people who routinely lift weights for a living, recreation, exercise or as a necessity do not have adequate protection against spine injury. Turn buckle and screws are mechanical devices which are widely used for creating both tension and compression loads. The present invention uses the property of a screw particularly a turn buckle, a type of screw to partially solve a big health problem of the world. The invention consists of a device for decompression and traction of a spine of a wearer, the device comprising a vest comprising a top section, a bottom section, a middle section, a turn buckle and a force measuring device.

The top section of the vest is positioned and tightened around an upper torso, passing through the arm pits, the bottom section of the vest is positioned and tightened around a lower torso at the waist line just above the sacrum. The back of the top section which covers the right and left scapula has a pocket to selectively receive the top screw rod of the turn buckle and the back of the bottom section which covers the lumbo-sacral area has a second pocket to selectively receive the bottom screw rod of the turn buckle.

The force measuring device is integrally but detachably tied between the two ends of the turn buckle in such a manner that zero reading is adjusted for each user depending on the physical dimensions of the user and distance between the top section and the bottom section. With both top and bottom sections tightened, the turn buckle positioned and the force measuring device tied and adjusted to zero, the turn buckle is then turned by wearer's hands to start inserting upward force on the upper belt of the vest and downward force on the lower belt of the vest. The amount of tensile force imposed on the spine by the turn buckle is measured by the force measuring device. It is clearly evident that the spine is subjected to tensile force thus making the decompression possible. The tensile force can be self adjusted by the user.

The invention is expected to save substantial amount of healthcare money worldwide both at personal and government levels and prevent future spine injuries by providing support and protection against weight lifting activities.

DETAILED DESCRIPTION OF THE INVENTION

Figure 1:
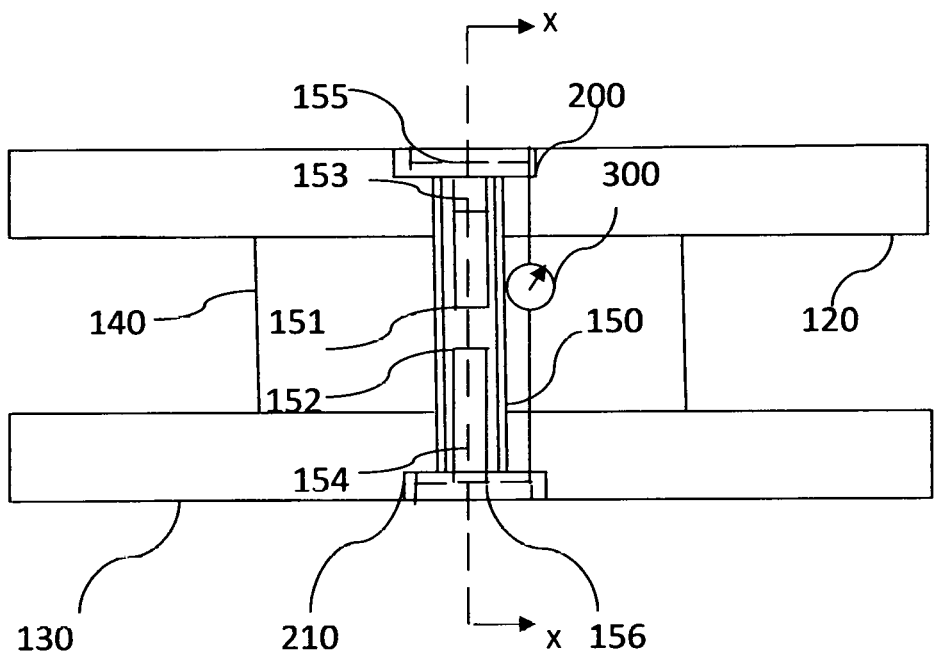
FIG. 1 is a schematic Plan View of Vest to Provide Decompression and Traction for Spine and Method of Use, as viewed from the back of the user.
Figure 2:
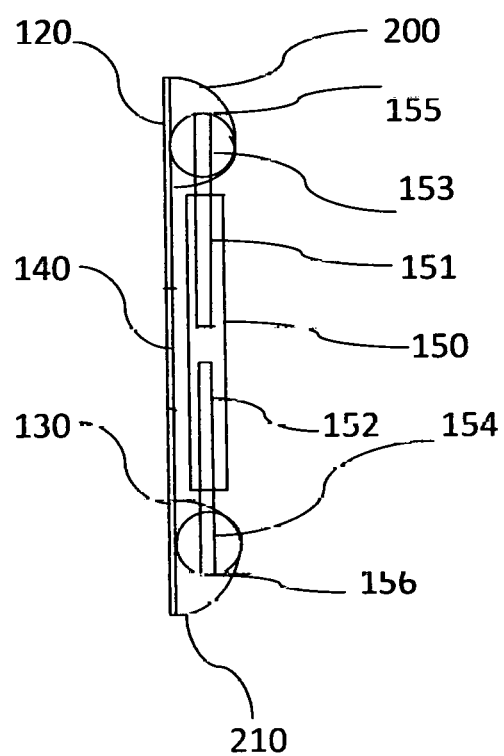
FIG. 2 is a schematic Cross-Sectional View along X-X line of FIG. 1 of Vest to Provide Decompression and Traction for Spine and Method of Use, as viewed from the left side of the user.

Referring now to the drawings of FIG. 1 and FIG. 2, Vest to Provide Decompression and Traction for Spine and Method of Use, for providing tensile force to spine (decompression and traction) and to enhance the load carrying capacity of the spine and provide additional insurance to the spine against injury during load carrying operations without hurting the spine; in accordance with the invention broadly includes a vest 10; the top section 120 of the vest 10; the bottom section 130 of the vest 10; the middle section 140 of the vest 10; the turn buckle 150; the top end of the top rod 153 of the turn buckle 150; the bottom end of the bottom rod 154 of the turn buckle 150; the first round curved cylinder 155; the second round curved cylinder 156; the pocket 200 outside of the top section 120 of the vest 10; and the pocket 210 outside the bottom section 130 of the vest 10.

As shown in FIG. 1 and FIG. 2, the top section 120 of the vest 10, the bottom section 130 of the vest 10, the middle section 140 of the vest 10, the pocket 200 outside of the top section 120 of the vest 10, and the pocket 210 outside of the bottom section 130 of the vest 10 collectively and integrally constitute the vest 10. The major materials the vest 10 is made of are strong synthetic fabrics similar to college back packs and air plane travel luggage. All the parts of the vest 10 are stitched together to make the vest 10 with strong twines durable and strong enough to withstand at least 100 lbs per square inch of pressure.

The turn buckle 150 is made of hard materials including but not limited to ordinary steel and plastics, and should have a size capable of withstanding a maximum of 100 lb force on the each of the two screw rods, designated as the top rod 151 and the bottom rod 152. The top end 153 of the top rod 151 is integrally and perpendicularly attached to a first round curved cylinder 155 to distribute the tensile force imposed by the turn buckle 150 on the thorax to a wider area. The bottom end 154 of the bottom rod 152 is integrally and perpendicularly attached to a second round curved cylinder 156 to distribute the tensile force imposed by the turn buckle 150 on the lumbar to a wider area.

During the use of the vest 10, the user positions the vest 10 such that the top section 120 rests against the thorax with the top of this section resting against the arm pits, and the bottom section 130 rests against the waist line with the bottom of this section resting against approximately in the middle of sacrum bone. After appropriately positioning the vest 10 on the torso, the top section 120 is firmly lightened to keep slippage of the top section to a minimum by using the Velcro provided in the top section. After appropriately positioning the vest 10 on the waist, the bottom section 130 is also tightened to keep the slippage of the bottom section to a minimum by using the Velcro provided in the bottom section. The middle section 140 of the vest 10 is meant to connect the top and the bottom sections together into a single vest to make the vest easy to use, and is made of elastic material to allow movement of the top and bottom section with respect to each other.

After wearing and tightening the vest, the turn buckle 150 is positioned on the back side of the vest in parallel with the spine, with the top end 153 of the top rod 151 and the curved cylinder 155 inside the pocket 200 and with the bottom end 154 of the bottom rod 152 and curved cylinder 156 inside the pocket 210. The force measuring device 300 is integrally but detachably tied between the two ends 153 and 154 of the turn buckle 150 in such a manner that device reads zero force after the vest is appropriately positioned on the torso. With the vest 10 tightened, the turn buckle 150 positioned and the force measuring device 300 tied; the turn buckle 150 is then gradually turned to start inserting upward force on the top section of the vest and downward force on the bottom section of the vest. The amount of tensile force imposed on the spine by the turn buckle is measured by the force measuring device 300. It is clearly evident that the spine is subjected to tensile force thus making the decompression and traction possible. The amount of applied tensile force can be self adjusted by the user.

I claim:

1. A device for decompression and traction of a spine of a wearer, the device comprising:
   a vest comprising:
      a top section configured to be adjustably tightened around an upper torso portion of the wearer;
      a bottom section configured to be adjustably tightened around a lower torso portion of the wearer; and
      a middle section stitched to a bottom edge of the top section and a top edge of the bottom section, the middle section being made of an elastic material to allow the top section to move relative to the bottom section;
   a turn buckle having a top screw rod and a bottom screw rod, the turn buckle being detachable from the vest; and
   a force measuring device detachably connected between the top and bottom screw rods configured to measure an amount of tensile force imposed on the spine in response to the turn buckle being turned when the device is secured to the wearer.

2. The device of claim 1, wherein the top section has a first pocket configured to selectively receive the top screw rod and the bottom section has a second pocket configured to selectively receive the bottom screw rod.

3. The device of claim 2, wherein the first and second pockets are located in a back of the device and the turn buckle is configured to be positioned on the back of the wearer parallel to the spine.

4. The device of claim 1, wherein top and bottom sections can be independently adjusted about the wearer.

5. A method for using the device of claim 2, comprising:
   tightening the top section of the vest about the wearer below the left and right arm pits;
   tightening the bottom section of the vest about the wearer just above the sacrum;
   positioning the turn buckle on the vest by placing the top screw rod in the first pocket and placing the bottom screw rod in the second pocket;
   with the vest tightened about the wearer, securing the force measuring device between the top and bottom screw rods; and
   gradually turning the turn buckle to create a desired amount of upward force on the top section and downward force on the bottom section thus imposing tensile force on the spine.

* * * * *